United States Patent [19]

Slinkard et al.

[11] 4,328,365

[45] May 4, 1982

[54] HYDROCARBON OXIDATION VIA CARBON MONOXIDE REDUCED CATALYST

[75] Inventors: William E. Slinkard, Corpus Christi, Tex.; Anthony B. Baylis, Berkeley Heights, N.J.

[73] Assignee: Celanese Corporation, New York, N.Y.

[21] Appl. No.: 198,699

[22] Filed: Oct. 20, 1980

Related U.S. Application Data

[63] Continuation of Ser. No. 65,663, Aug. 10, 1979, abandoned, which is a continuation-in-part of Ser. No. 859,898, Dec. 12, 1977, abandoned.

[51] Int. Cl.³ .......................... C07B 3/00; C07C 53/08
[52] U.S. Cl. ................................ 562/512.2; 562/536; 562/548; 562/549; 568/956
[58] Field of Search ............ 562/548, 549, 536, 512.2; 568/956

[56] References Cited

U.S. PATENT DOCUMENTS

| | | | |
|---|---|---|---|
| 1,286,256 | 12/1918 | Dreyfus | 562/536 |
| 2,379,760 | 2/1945 | Standinger et al. | 562/536 |
| 2,995,528 | 8/1961 | Dowden et al. | 562/549 |
| 3,907,833 | 9/1975 | Slinkard et al. | 562/549 |
| 3,948,983 | 4/1976 | Hackmann et al. | 562/548 |
| 3,997,602 | 12/1976 | Taylor | 562/549 |
| 4,052,417 | 10/1977 | Slinkard et al. | 562/549 |

FOREIGN PATENT DOCUMENTS 166670  12/1964  U.S.S.R. ............... 562/549

*Primary Examiner*—Howard T. Mars
*Attorney, Agent, or Firm*—Linn I. Grim

[57] ABSTRACT

The present invention provides a supported catalyst for use in a vapor phase reaction for the high yield conversion of lower aliphatic hydrocarbons such as butane to corresponding monocarboxylic acids such as acetic acid. The catalyst is prepared by the carbon monoxide reduction of a vanadium pentoxide-impregnated, inert porous carrier.

8 Claims, No Drawings

HYDROCARBON OXIDATION VIA CARBON MONOXIDE REDUCED CATALYST

This is a continuation of application Ser. No. 065,663, filed Aug. 10, 1979, which is a continuation-in-part of application Ser. No. 859,898, filed Dec. 12, 1977, both now abandoned.

BACKGROUND OF THE INVENTION

Processes for producing lower aliphatic monocarboxylic acids such as acetic acid by the vapor phase oxidation of lower aliphatic hydrocarbons are known. For example, acetic acid is prepared by the vapor phase oxidation of butane according to the following equation:

$$C_4H_{10} + 5/2\ O_2 \rightarrow 2CH_3COOH + H_2O$$

However, processes for the oxidation of hydrocarbons in the vapor phase by means of oxygen-containing gases have not proven entirely satisfactory primarily due to the excessive formation of undesirable carbon oxides, and to the difficulty in maintaining control of the highly exothermic oxidation reaction. U.S. Pat. No. 3,395,159 provides an improved process wherein the oxidation of hydrocarbons is performed in a reactor system having fused vanadium oxide catalyst coated on the inner surface of the reactor, which system has the advantage of better temperature control and isothermal operation. The use of early catalysts such as vanadium pentoxide, either supported or unsupported, for the vapor phase oxidation of lower aliphatic hydrocarbons generally results in yields and process efficiencies which fall substantially short of theoretical potential. Also, the resulting products are often impure due to a lack of selectivity when such catalysts are employed.

Neat (i.e., unsupported) reduced vanadium oxides such as vanadium tetroxide have been suggested as a remedy for the above disadvantages but heretofore the use of the catalysts in the vapor phase oxidation of lower aliphatic hydrocarbons has resulted in inefficient processes which lack a high degree of selectivity. Furthermore, reduced vanadium oxides in neat form (pellets) lose crush strength during use. This is extremely critical for if the loss of crush strength is excessive such that extensive catalyst fines are developed, the pressure drop over the reactor will become too great to operate the unit thus requiring the catalyst to be removed and recharged. This, of course, is an expensive and time-consuming operation that may result in the whole process being too uneconomical to be commercially feasible.

One way to eliminate this crush strength loss is to support the reduced vanadium oxide on an inert and rigid carrier.

Typical of the elaborate steps taken to obviate the crush strength loss via a carrier is the procedure disclosed in U.S. Pat. No. 3,962,137 wherein an abrasion resistant catalyst is produced for the oxidation of lower aliphatic hydrocarbons by intimately mixing an aqueous suspension of colloidal non-porous silica particles with a water soluble metal salt which is decomposable by heat to a metal oxide, calcining the mixture, adding a further amount of the aqueous suspension of colloidal non-porous silica particles, and drying this catalyst composition. The essence of this patented invention is the formation of an outer porous net of non-porous colloidal silica particles over the calcined mixture of metal oxide and non-porous colloidal silica.

OBJECTS AND SUMMARY OF THE INVENTION

Accordingly, a general object of the present invention is to avoid or substantially alleviate the above problems of the prior art in a simple and straightforward manner.

A more specific object is the provision of a process for the production of acetic acid by the vapor phase oxidation of lower aliphatic hydrocarbons.

Another object is to provide a highly efficient process for the production of acetic acid by the vapor phase oxidation of lower aliphatic hydrocarbons using a catalyst which has significantly improved physical strength.

Since selectivity in the vapor phase oxidation of lower aliphatic hydrocarbons to acetic acid is almost proportional to the amount of reduced vanadium oxide present, yet another object is to provide a method of achieving increased vanadium oxide loadings on an inert carrier.

These and other objects are achieved by a process for preparing acetic acid by the vapor phase oxidation of a lower aliphatic hydrocarbon such as butane, which process comprises reacting the lower aliphatic hydrocarbon and an oxygen-containing gas in the vapor phase, preferably in the presence of steam, and a catalytic amount of carbon monoxide (CO) reduced vanadium pentoxide ($V_2O_5$) impregnated onto an inert porous support.

The essence of the invention lies in the discovery that CO reduction of an inert porous support which has been impregnated $V_2O_5$ to give $V_2O_5$ loadings in excess of 50 weight percent yields an extremely crush-resistant catalyst which, when utilized in a vapor phase oxidation of a lower aliphatic hydrocarbon such as butane, realizes high efficiency to acetic acid; low efficiency to butenes and rapid conversion of recycled butenes to acetic acid which avoids butene buildup within the reactor. Furthermore, since the temperatures and pressures needed for the CO reduction step are well within the operating capability of commercial vapor-phase oxidation reactors, the supported vanadium oxide catalyst can be reduced or regenerated in situ without having to remove the catalyst from the reactor tubes.

Other objects and advantages of the present invention will become apparent from the following description of the preferred embodiments.

DESCRIPTION OF THE PREFERRED EMBODIMENTS

The first step in the preparation of the catalyst of the instant invention is to impregnate a highly porous, predominantly inert support with vanadium pentoxide ($V_2O_5$). Techniques to accomplish this with high loadings are well known in the art. For example, the inert supports can be impregnated with aqueous solutions of soluble vanadium salts such as vanadyl oxalate, ammonium meta-vanadate or decavanadate; dried, and then calcined in an oxygen-containing gas such as air to produce the vanadium pentoxide impregnated starting support. A preferred method for generating this $V_2O_5$ impregnated support is to physically mix $V_2O_5$ powder with high surface area silica catalyst supports such as Houdry's macroporous silica beads or a silicon carbide and increase the temperature until the $V_2O_5$ is molten. The amount of $V_2O_5$ present should be such as to avoid agglomeration of the impregnated beads. When all of the $V_2O_5$ has been absorbed by the support, the catalyst precursor is cooled to room temperature. The $V_2O_5$ impregnated support is then subjected to a carbon monoxide atmosphere at temperatures high enough to effect reasonable reduction rates yet below about 600° C. to avoid remelting the $V_2O_5$. This process is continued until all of the $V_2O_5$ is in a reduced state as can be determined by carbon dioxide ($CO_2$) measurements in the vent gases. Of course, if the CO reduction is accomplished under elevated pressures such as for example from about 150 to about 250 psig, the reduction times are significantly reduced.

In the process of the present invention a lower aliphatic hydrocarbon is reacted with an oxygen-containing gas in the presence of a catalytically effective amount of the above-described reduced vanadium oxide supported catalyst to produce acetic acid.

By "lower aliphatic hydrocarbon" is meant any saturated or unsaturated aliphatic hydrocarbon containing from 2 to 10 carbon atoms. These lower aliphatic hydrocarbons include alkanes, alkenes and alkynes such as ethylene, propylene, butene, propane, butane, pentene, octane, and their isomers. Particularly preferred aliphatic hydrocarbons are the alkanes and alkenes including propane, butane, butene, isobutane, isobutene and mixtures thereof.

The production of acetic acid from butane can give particularly advantageous results.

By the term "reduced vanadium oxide or reduced vanadium pentoxide" is meant a vanadium oxide in which the average vanadium ion valency is less than 5. A lower oxidation state of vanadium ions is an essential feature of the present invention catalysts. This is based on the observation that vanadium pentoxide (i.e., a catalyst containing vanadium ions with a valence of 5) is not an active catalyst under the process conditions to be described, and it is, therefore, advantageous to exclude vanadium pentoxide from the catalyst compositions to the greatest extent possible.

The reduced vanadium oxides employed in the catalysts of the present invention are all intermediate in average oxidation states, i.e., between $V_2O_5$ and $V_2O_3$. Although the initial charge can contain $V_2O_5$ and $V_2O_3$, X-ray diffraction studies confirm that vanadium oxide catalysts operable in the process are effectively expressed empirically as $V_3O_5$, $V_4O_7$, $V_5O_9$, $V_6O_{11}$, $V_7O_{13}$, $V_2O_4$ and/or $V_6O_{13}$. The average valence of the vanadium ions in these oxides generally ranges from 3 to about 4.5.

The oxygen necessary as a reactant in the present process may be from practically any molecular oxygen-containing gas such as molecular oxygen or air. Also, the molecular oxygen-containing gas may be one wherein molecular oxygen is mixed in varying amounts with an inert diluent gas such as nitrogen, argon, or a carbon oxide. The lower aliphatic hydrocarbon and oxygen-containing gas can be reacted within a wide range of molar ratios. However, it is an essential feature of the invention process that the quantity of oxygen gas in the feed stream be the least required to convert efficiently the hydrocarbon stream to acetic acid consistent with necessary temperature control and retention of catalyst activity. It is important that the vanadium oxide catalyst is not oxidized to vanadium pentoxide. Even the presence of a small amount of vanadium pentoxide is effective in reducing the yield of acetic acid. The quantity of oxygen gas in the feed stream usually is maintained in the range between about 0.05 and 1 moles per mole of lower aliphatic hydrocarbon. At elevated pressures, the preferred range is from about 0.05 to about 0.30.

In a preferred embodiment of the invention process, water is included in the feed stream in a quantity between about 0.1 and 2.0 moles per mole of lower aliphatic hydrocarbon. The presence of water vapor in the oxidation reaction system can increase the yield of acetic acid by as much as 10 percent in the case where the hydrocarbon feed stream is normal butane.

The present process is carried out at a temperature generally between about 180° and about 400° C., typically between about 200° and about 350° C., and preferably between about 220° and about 300° C.

The present process can be carried out at subatmospheric, atmospheric, or super atmospheric pressures, generally from about 0.1 to about 50 atmospheres, typically from about 0.5 to about 30 atmospheres, and preferably from about 1 to about 20 atmospheres.

The contact time of the reactants with the catalyst is generally between about 0.1 and 100 seconds, typically between about 0.25 and 50 seconds. By contact time as used herein, is meant the contact time adjusted to 25° C. and 1 atmospheric pressure (i.e., standard temperature and pressure, denoted STP). Thus, the contact time is calculated by dividing the volume of the catalyst bed (including voids) by the volume per unit time flow rate of the reactants at STP.

The process of the present invention may be carried out continuously and the catalyst may be present in various forms such as in one or more fixed beds or as a fluidized system.

Portions of the reactants which do not undergo reaction may be recycled if necessary. Selected intermediate products, such as butenes and acetaldehydes, are preferably recycled also. The desired acetic acid product may be separated from any impurities by condensation followed by fractionation and aqueous or non-aqueous extraction of the product from the unreacted lower aliphatic hydrocarbon.

In this specification, the terms conversion and efficiency are defined as follows:

$$\text{conversion, \%} = \frac{\text{moles lower aliphatic hydrocarbon or oxygen converted}}{\text{moles lower aliphatic hydrocarbon or oxygen fed}} \times 100$$

$$\text{\% carbon efficiency to component } i = \frac{\text{moles component } i \text{ formed} \times \text{carbon atoms per mole of component } i}{\text{total moles of carbon in all products analyzed}} \times 100$$

Acetic acid is generally produced by the present process with a conversion (based on oxygen) generally of at least 90 percent, often at least about 95 percent, a conversion based on lower aliphatic hydrocarbon (which, as noted above, is present in substantial excess) generally of at least about 1 percent, typically from about 3 to about 5 percent, and a carbon efficiency of generally at least about 50 percent, typically at least about 55 percent, often at least about 60 percent with recycled intermediates.

As indicated hereinabove, the present process is useful for preparing acetic acid with improved yield and process efficiency with a catalyst of superior crush strength. The recovery of the product stream and the separation of the acetic acid from the acetaldehyde, maleic acid and other by-products can be accomplished by conventional procedures. U.S. Pat. No. 3,624,148 describes a method for the separation of acetic acid from maleic acid.

The present invention is further illustrated by the following examples. All parts and percentages in the examples as well as in the specification and claims are by weight unless otherwise specified. The reactants and other specific ingredients are presented as being typical, and various modifications can be devised in view of the foregoing disclosure within the scope of the invention.

CATALYST PREPARATION

The following two examples illustrate the preferred method for making the catalysts of the instant invention.

EXAMPLE I 600 grams of $V_2O_5$ powder is physically mixed with 261 grams of silica beads, placed in a quartz calcining dish, and heated to 816° C. The mixture is held at that temperature for about 16 hours and then allowed to cool to room temperature. Nearly all of the $V_2O_5$ is absorbed into the silica beads (about $\frac{1}{8}''$ to $\frac{1}{4}''$ in diameter).

The supported $V_2O_5$ on silica is placed in the center of a two inch diameter quartz tube, flushed with carbon monoxide, and heated to 200° C. The temperature is increased from 200° to 500° C. over a period of 5 hours, kept at 500° C. for about 116 hours, and then cooled rapidly to room temperature—still under a steady stream of carbon monoxide.

EXAMPLE II 310 grams of $V_2O_5$ is poured over 151 grams of silica beads in two large quartz dishes heated to 816° C. and held at that temperature for about 16 hours. The dishes are removed from the oven and cooled rapidly to room temperature. The $V_2O_5$ is melted and absorbed by the beads (about $\frac{1}{8}''$ to $\frac{1}{4}''$ in diameter) to yield free flowing yellow beads. Six batches of the above are prepared and combined.

1500 grams from the above $V_2O_5$ impregnated silica beads are placed in a one inch diameter pyrex tube and thoroughly flushed with carbon monoxide. The material is heated to 500° C. over a 3 hour period; held at that temperature for 136 hours; and then cooled to room temperature still under one atmosphere of carbon monoxide.

EXAMPLE III 300 grams of the $V_2O_5$ impregnated silica beads are also activated by subjecting the beads to a temperature of 275° C. while under a carbon monoxide blanket at pressure of from about 150 to 190 psig. The $V_2O_5$ is completely reduced, i.e., activated in about 16 hours.

EXAMPLE IV

This example illustrates the use of the preferred catalyst in the vapor phase oxidation of lower aliphatic hydrocarbons to acetic acid.

A $\frac{3}{4}''$ schedule 40 steel pipe is employed to hold the catalyst charge. The pipe is about 10 feet long with an inside diameter of about 0.82 inches. The usual catalyst charge is about 500 cc of spherical or pelleted catalyst. Silicon carbide spheres or pellets are used in front of the catalyst to serve as a preheat zone for the reactant gases. The reactor is heated to the desired temperature using pressurized steam. Flow rates of the lower aliphatic hydrocarbons and air (or oxygen) are determined by mass flowmeters. Steam is introduced as water at a known flow rate and flashed to steam with the flow rate of steam calculated by application of the ideal gas law. After the flow rates are stabilized, the temperature of the reactor (initially about 240° C.) is then slowly raised until the desired oxygen conversion rate is achieved. Material balances are then obtained at this temperature.

Reactions can be conducted at or near atmospheric pressure but it is preferred to operate the reactor under pressures so that cooling water can be used to condense the butane recycle stream.

Analysis of the vent gas stream entails passing the reaction products plus unreacted lower aliphatic hydrocarbon and steam through a water-cooled condenser after leaving the heated reaction zone to remove the liquid products and water from the vent stream. The vent stream, leaving the condenser, now containing primarily lower aliphatic hydrocarbons, carbon oxides, and nitrogen is analyzed by standard gas chromatographic techniques. Components analyzed include butane, butenes, acetaldehyde, oxygen, nitrogen, carbon monoxide, and carbon dioxide. The liquid sample is collected after the end of the run and analyzed by standard gas chromatographic techniques. Components analyzed include: acetic acid, acetaldehyde, acetone, maleic acid, acrylic acid, propionic acid, butyric acid, formaldehyde, formic acid, methyl ethyl ketone, and butanol.

The following represents typical results realized when the catalyst of Example I is utilized on the above-described process.

| Reactor Pressure (psig) | 180 |
| --- | --- |
| Reactor Temperature (°C.) | 275 |
| Feed Stream (Mol Ratio) | |
| $C^e_4:O_2:H_2O$ | 9.0:1.0:9.5 |
| Total Feed Rate | |
| 1/min (STP) | 26.95 |
| Butane Conversion (%) | 3.8 |
| Oxygen Conversion (%) | 96 |
| Carbon Efficiency (%) | |
| Butenes | 24 |
| Acetic Acid | 42 |
| Acetaldehyde | 3.8 |
| Carbon Oxides | 23 |

EXAMPLE V

The following represents typical results when the catalyst of Example II is utilized in the process of Example IV. The test is conducted in an 18 foot pipe (0.78 inch inside diameter) using about 1700 cc of catalyst.

| Reactor Pressure (psig) | 180 |
| --- | --- |
| Reactor Temperature (°C.) | 275 |
| Feed Stream (Mol Ratio) | |
| $C_4^e:O_2:H_2O$ | 7.8:1:3.7 |
| Total Feed Rate | |
| 1/min (STP) | 172.4 |
| Butane Conversion (%) | 3.15 |
| $O_2$ Conversion (%) | 98 |
| Carbon Efficiency (%) | |
| Butenes | 13 |
| Acetic Acid | 46 |
| Acetaldehyde | 6.2 |

| | |
|---|---|
| -continued | |
| Carbon Oxides | 28 |

EXAMPLE VI

The following shows the superior crush strength of the instant catalysts. After the run of Example V is completed (1000 hours) the catalyst is tested at various bed depth levels.

For comparison purposes, the average crush strength of an unused portion of this catalyst is 21.6 lbs.

| Distance into Bed (%) | Percent Fines in Sample (wt. %) | Av. Crush Strength, lbs. (Range) |
|---|---|---|
| 6.7–13.9 | 0.03 | 23.8 |
| 13.9–20.6 | 0.01 | 25.0 |
| 31.1–35.6 | 0.02 | 22.4 |
| 46.1–51.1 | 0.02 | 23.9 |
| 61.1–66.1 | 0.04 | 17.9 |
| 76.1–80.6 | 0.04 | 17.7 |
| 84.4–88.3 | 0.07 | 20.4 |
| 92.8–96.7 | 0.09 | 20.2 |
| 96.7–100 | 0.10 | 22.3 |

Typical crush strength measurements for bulk unsupported reduced vanadium oxide catalyst (prepared by the thermal decomposition of vanadyl oxalate) are as follows:

| | |
|---|---|
| Unused: | 10–15 lbs. |
| Used (300 + hrs): | 2–3 lbs. |

EXAMPLES VII AND VIII

Samples of $V_2O_5$ impregnated on porous silica beads are prepared as in Examples I and II. One half of these samples are activated by subjecting the beads to a hydrogen flush while heating the material to 500° C. over a 3 hour period. The material is held at that temperature for 136 hours and then cooled to room temperature while still under a blanket of an atmosphere of hydrogen (Example VII).

The other half of the $V_2O_5$ impregnated silica beads are activated by subjecting the beads to an ethanol saturated nitrogen purge while heating the material to 500° C. over a 3 hour period. The material is held at that temperature for 136 hours and then cooled to room temperature while still under a blanket of one atmosphere of ethanol saturated nitrogen (Example VIII).

EXAMPLE IX TO XIII

The following illustrates the unexpectedly improved results realized when using the catalysts of the instant invention (Examples I–III) i.e. the CO reduced $V_2O_5$ impregnated beads, as compared to $V_2O_5$ impregnated beads which had been reduced with hydrogen (Example VII) or ethanol (Example VIII) in the process of Example IV.

Furthermore, acetic acid efficiency figures are provided to illustrate the increased carbon efficiency realized when the butenes are recycled into the feed stream. Of course, acetaldehyde recycle into the feed stream, in addition to the butenes, would increase acetic acid efficiencies even more.

Thus, as can be seen from the above, with similar overall conversions, catalysts reduced with CO give significantly improved selectivity to acetic acid and at the same time give significantly less butane to butene conversion with its attendant carbon by-product formation.

While all of the above runs are conducted with a fixed bed reactor, it is quite obvious that the superior crush strength of the instant catalyst makes it ideally suited for fluid bed operations.

We claim:

1. A process for preparing acetic acid by the vapor phase oxidation of lower aliphatic hydrocarbons which process comprises reacting the lower aliphatic hydrocarbon feed stream comprising alkanes with an oxygen-containing gas in the vapor phase in the presence of steam and a catalytic amount of a catalyst consisting of reduced vanadium oxide supported on an inert porous carrier, said catalyst having been activated by the carbon monoxide reduction of vanadium pentoxide-impregnated inert porous carrier, said catalyst having in excess of 50 weight percent of vanadium pentoxide prior to said reduction.

2. The process of claim 1 wherein the molar ratio of oxygen to lower aliphatic hydrocarbon is from about 0.05 to 0.30.

3. The process of claim 1 wherein the molar ratio of steam to lower aliphatic hydrocarbon is from about 0.1 to 2.0.

EXAMPLES IX TO XIII

| Catalyst Identification | Activating or Reducing Agent | Reactor Temp., °C. | Butane: $O_2:H_2O$ Moles | Conversion, % | | Carbon Efficiency, % | | | | Acetic Acid Efficiency on Butene Recycle |
|---|---|---|---|---|---|---|---|---|---|---|
| | | | | $O_2$ | Butane | Acetic Acid | Acetaldehyde | CO + $CO_2$ | Butene | |
| 59 wt % $V_2O_5$ on $SiO_2$ | CO | 242 | 20:1:8 | 100 | 1.7 | 45 | 2.3 | 24 | 27 | 62 |
| 60 wt % $V_2O_5$ on $SiO_2$ | $H_2$ | 242 | 20:1:8 | 100 | 2.0 | 34 | 2.0 | 23 | 38 | 55 |
| 62 wt % $V_2O_5$ on $SiO_2$ | CO | 267 | 10:1:9 | 97 | 3.6 | 43 | 4.5 | 25 | 21 | 54 |
| 65 wt % $V_2O_5$ on $SiO_2$ | CO | 275 | 9:1:10 | 95 | 3.9 | 41 | 3.7 | 23 | 25 | 54 |
| 64 wt % $V_2O_5$ on $SiO_2$ | Ethanol | 270 | 10:1:9 | 91 | 3.9 | 35 | 5.5 | 27 | 27 | 48 |

4. The process of claim 1 wherein the temperature of the process is from about 220° to about 300° C.

5. The process of claim 1 wherein the pressure of the process is from about 1 to about 20 atmospheres.

6. The acetic acid reaction of claim 1 wherein the alkane is n-butane.

7. The process of claim 1 wherein the lower aliphatic hydrocarbon feed stream contains recycled butenes from the vapor phase oxidation reaction of claim 1.

8. The process of claim 1 wherein the lower aliphatic hydrocarbon feed stream contains recycled butenes and acetaldehyde from the vapor phase oxidation reaction of claim 1.

* * * * *